US006238880B1

(12) United States Patent
Moine et al.

(10) Patent No.: US 6,238,880 B1
(45) Date of Patent: May 29, 2001

(54) METHOD FOR PROTEIN STABILIZATION OF WINES

(75) Inventors: Virginie Moine, Pessac; Denis Dubourdieu, Beguey, both of (FR)

(73) Assignee: Societe d'Applications de Recherches et de Conseils Oenologiques, Bordeaux (FR)

( * ) Notice: Subject to any disclaimer, the term of this patent is extended or adjusted under 35 U.S.C. 154(b) by 0 days.

(21) Appl. No.: 09/214,118

(22) PCT Filed: Jun. 25, 1997

(86) PCT No.: PCT/FR97/01130

§ 371 Date: Jan. 25, 1999

§ 102(e) Date: Jan. 25, 1999

(87) PCT Pub. No.: WO97/49794

PCT Pub. Date: Dec. 31, 1997

(30) Foreign Application Priority Data

Jun. 26, 1996 (FR) .................................. 96 08187

(51) Int. Cl.$^7$ ....................................... C12P 21/06
(52) U.S. Cl. ................. 435/68.1; 435/200; 435/219; 426/12
(58) Field of Search ................ 426/60, 12, 330.4, 426/592; 435/7.31, 7.4, 200, 68.1

(56) References Cited

FOREIGN PATENT DOCUMENTS

| 2 726 284 | 5/1996 | (FR) . |
| 49 001 870 | 1/1974 | (JP) . |
| 8-103271 | 4/1996 | (JP) . |

Primary Examiner—Keith Hendricks
(74) Attorney, Agent, or Firm—Young & Thompson

(57) ABSTRACT

A process for the production of a biological product having a stabilization effect on the protein precipitations of white wines, characterized in that it consists in carrying out an enzymatic digestion of invertase of *Saccharomyces cerevisiae* by hydrolysis to obtain the biological product of stabilization.

5 Claims, 2 Drawing Sheets

METHOD FOR PROTEIN STABILIZATION OF WINES

CROSS REFERENCE TO RELATED APPLICATION

This is the 35 USC §371 national stage of PCT/FR97/01130 filed Jun. 25, 1997, which designated the United States of America.

FIELD OF THE INVENTION

The French present invention has for its object a product for the protein stabilization of wines.

In patent application No. 2,726,284 in the name of the Faculty of Oenology of Bordeaux, there have been described and claimed mannoproteins extracted enzymatically, whose action against precipitations of tartaric and protein salts is particularly effective.

More particularly, these mannoproteins were obtained by enzymatic digestion of the cell walls of yeast, under the action of $\beta$1–3 and $\beta$1–6 glucanases, said yeasts being, in one embodiment, the species *Saccharomyces cerevisiae.*

It has also been determined that the mannoprotein of a molecular mass of 31,800 Daltons, called MP32, was more particularly effective, for protein stabilization.

Also, tests have shown that MP32 is a fragment of invertase.

SUMMARY OF THE INVENTION

The invention thus relates to a procedure for obtaining mannoproteins enzymatically, from invertase, for the protein stabilization of white wines, which consists in carrying out an enzymatic digestion of invertase of *Saccharomyces cerevisiae* by hydrolysis.

This enzymatic digestion is carried out in the presence of $\beta$ 1–3 and $\beta$ 1–6 glucanase and the active proteases, is acid media.

The hydrolysate recovered is subjected to a physical treatment comprising particularly a dialysis against water, through a membrane with a cutoff threshold of 6,000 to 8,000 Daltons, followed by lyophilization with centrifugation and filtration prior to dialysis.

The invention also relates to the choice of cortexes of yeast adapted to have an invertase activity such as to generate mannoproteins of a molecular mass suitable to stabilize white wines.

The invention also relates to a process for treating a white wine for its protein stabilization, which consists in adding to this wine a hydrolysate of invertase of *Saccharomyces cerevisiae*, more particularly a quantity of the order of 25 g/hl of lyophilisate.

The invention also relates to the stabilization product obtained.

BRIEF DESCRIPTION OF THE INVENTION

Figure 1:
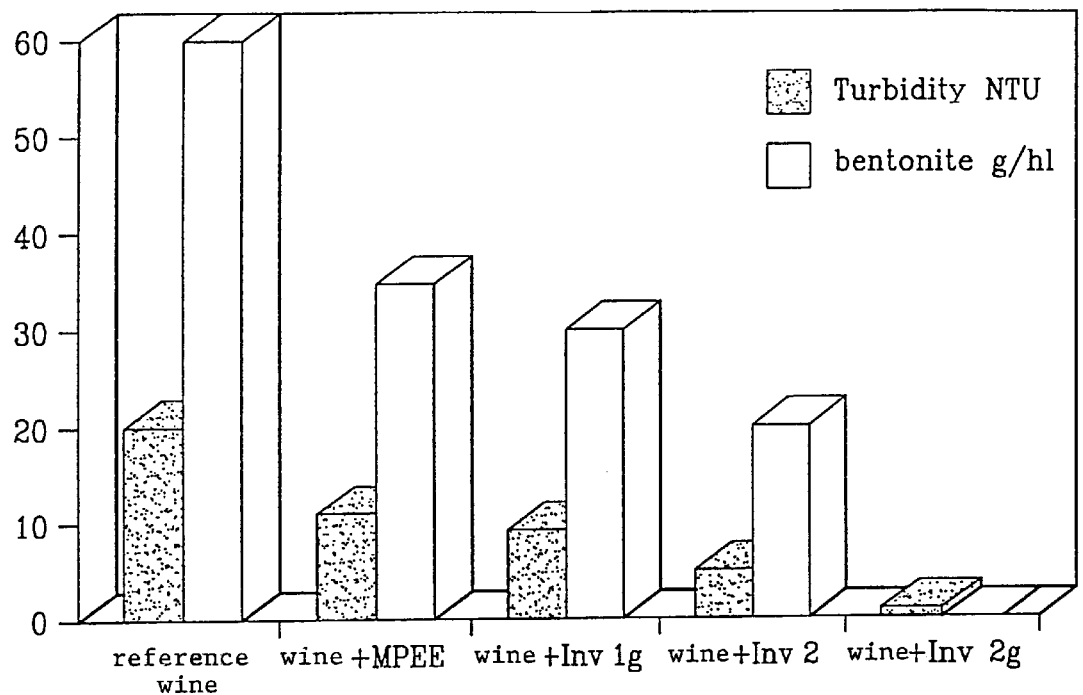
Figure 2:
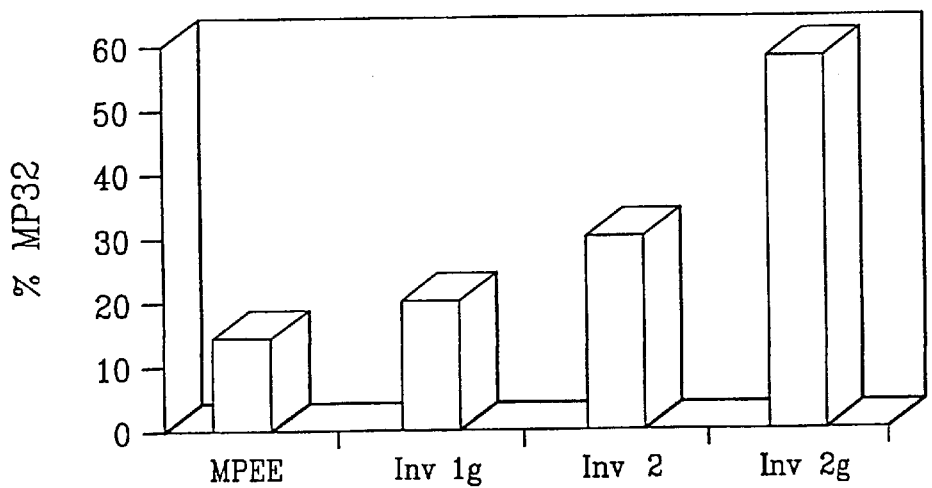
Figure 3:
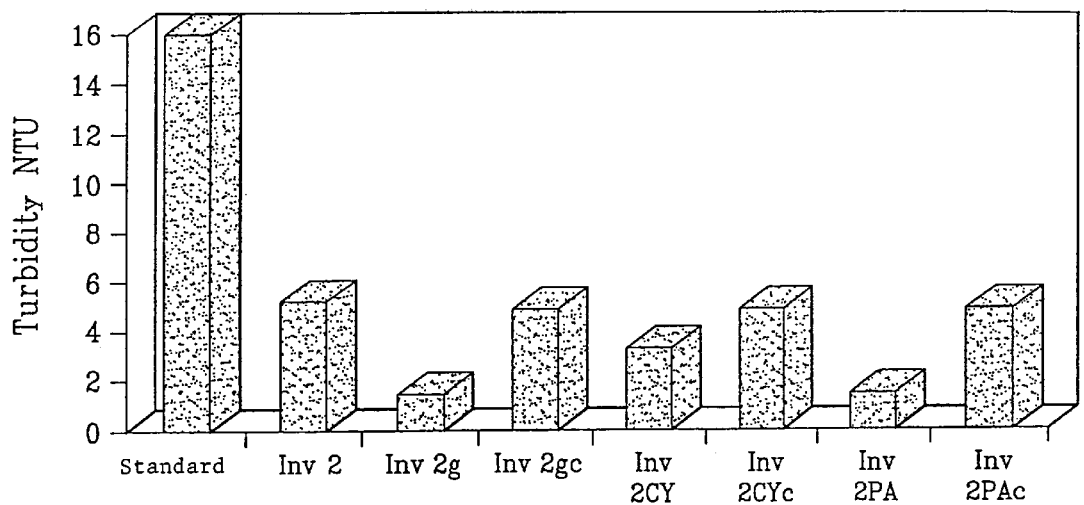
Figure 4:
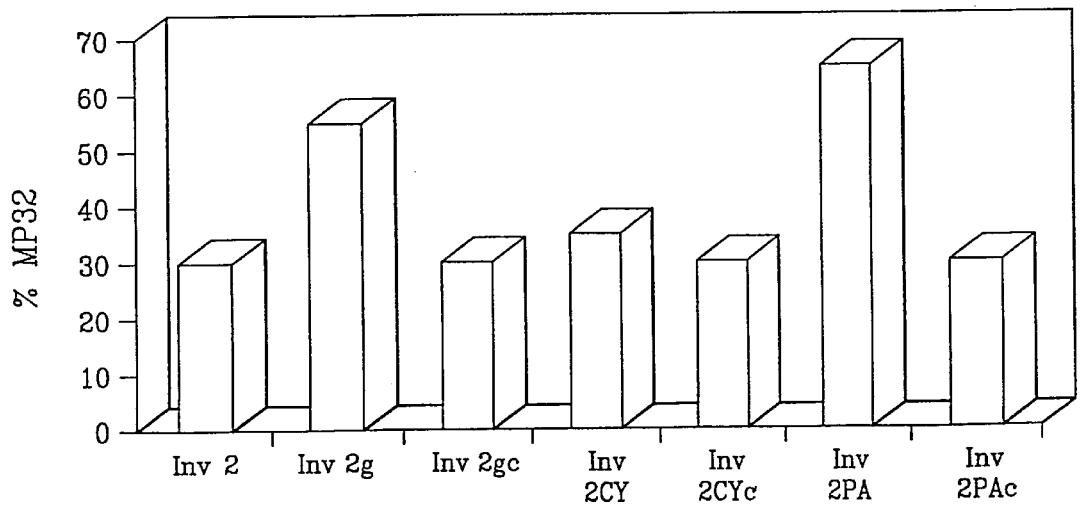

The process and the product obtained were the object of tests which are described hereinafter, with respect to the drawings, which show:

FIG. 1, a comparative diagram of the effect of stabilization obtained, by the quantity of bentonite necessary for the stabilization of the wine and by the turbidity index NTU, reflecting the density of the cloudiness formed after the test with heat, FIG. 2, a comparative diagram of the MP32 content of the different preparations, carried out by capillary electrophoresis, FIG. 3, a comparative diagram of the effect of stabilization obtained with the different preparations as a function of the types of invertase hydrolysates, and FIG. 4, the comparative MP32 content of the different preparations used to obtain the results of FIG. 3.

DETAILED DESCRIPTION OF THE INVENTION

It is known that invertase 2 or 4 of *Saccharomyces cerevisiae* has a molecular mass of 270,000 Daltons, which is much greater than the molecular mass of MP32.

It is also known that invertase comprises particularly the following amino acid sequences:

Lysine-Valine-Phenylalanine-Tryptophane-Tyrosine-Glutamine-Proline-Serine-Glutagine-Lysine.

Surprisingly, the applicants have carried out a sequencing of the mannoprotein MP32 and have noted 100% homology with the portion of the sequence contained in the invertase.

So as to verify that mannoprotein MP32 is indeed a fragment of invertase of *Saccharomyces cerevisiae*, it has been proposed to carry out the two following preparations:

Inv1, 30 to 50 units/mg of insoluble commercial invertase SIGMA®, hydrolyzed in 5% of Glucanex®, of the firm NOVO, and Inv2, 400 units/mg of soluble commercial invertase SIGMA®, hydrolyzed in 5% of Glucanex®, of the firm NOVO.

After digestion, the hydrolysates Inv1g and Inv2g are centrifuged, filtered and dialyzed with a membrane having a cutoff threshold of the order of 6,000 to 8,000 Daltons, the hydrolysate thus obtained is lyophilized.

There is then added 25 g/hl of each of the preparations to a wine so as to carry out a comparative test of the effect of stabilization of each of these preparations.

The results are shown in the diagram of FIG. 1, each wine having been subjected to a warm treatment, 80° C., for 30 minutes so as to evaluate the protein stability.

It has been determined that the mannoprotein extracted by an enzymatic method from the cell walls of yeast digested with Glucanex, has a stabilizing effect, because less bentonite is needed for an improved NTU turbidity index.

At a low concentration of invertase, the preparation of Inv1g is even better than the preparation extracted enzymatically from yeast cell walls.

There is noted an increased stabilization as soon as the concentration of invertase increases, even with the non-hydrolyzed preparation.

The stability is very greatly improved when, with a high initial concentration of invertase, Inv2 is hydrolyzed in Glucanex (Inv2g).

Thus, the richer the preparation is in invertase, the more active is its hydrolysate from Glucanex.

It is no longer necessary to add bentonite, and the formation of cloudiness at the end of the test under heat, is substantially zero.

By capillary electrophoresis, it can be determined that the content of MP32 increases parallel to the stabilizing activity. The more MP32 there is, the more the stabilizing activity is substantial.

It might be thought that the liberation of the invertase fragment of *Saccharomyces cerevisiae* in the course of autolysis of yeast, containing the suitable amino acid sequence, is due to the action of proteases.

Given the physical-chemical parameters of wines, pH 3 to 3.8, the only *Saccharomyces cerevisiae* proteases adapted to be active are:

protease A, SIGMA® and carboxypeptidase Y, SIGMA®.

The following tests were carried out:

In a citrate buffer solution of 10 ml, there is hydrolyzed 100 mg of purified invertase Inv2, for 15 hours at 20° C., with:

5 mg of Glucanex, 2.5 mg of carboxypeptidase Y, 0.3 mg of protease A.

In parallel, a similar hydrolysis is carried out, but with inactivation of these same enzymes with heat (1minute at 100° C.).

Then, a dialysis against water of the different preparations is conducted, with a membrane having as before a cutoff threshold of 6,000 to 8,000 Daltons, then they are lyophilized.

Identically, specimens of wine receive the preparations at the rate of 25 g/hl, then the wines are subjected to a test under heat so as to determine the turbidity index.

In the diagram of FIG. 3, the abbreviations correspond to the following products:

g, Glucanex gc, Glucanex, but previously inactivated at 100° C. for one minute,

CY, carboxypeptidase Y,

Cyc, carboxypeptidase Y, but previously inactivated at 100° C. for one minute,

PA, protease A, and

PAc, protease A, but previously inactivated at 100° C. for one minute.

It is seen that the enzymatic hydrolysis of a preparation of invertase produces products having stabilizing action on white wine.

Particularly noteworthy is the effectiveness of Glucanex and of protease A to generate mannoproteins MP32. Protease A is the most effective.

This is moreover confirmed by tests shown in FIG. 4, which show the content of MP32 of the different preceding hydrolysates.

It should also be noted that the partial deactivation by heat has a negative effect on the results obtained.

It has thus been shown that the process according to the invention provides a stabilizing action on proteins of white wines.

What is claimed is:

1. Process for the production of a biological product having a stabilizing effect on protein precipitations in white wines, which comprises:

carrying out an enzymatic digestion of invertase of *Saccharomyces cerevisiae* by hydrolysis in the presence of exogenous proteases in acid media; and recovering the hydrolysate.

2. The process according to claim 1, wherein the enzymatic digestion is carried out in the presence of β 1–3 glucanase and β 1–6 glucanase.

3. The process according to claim 1, wherein the recovered hydrolysate is subjected to a physical separation treatment.

4. The process according to claim 3, wherein the physical separation treatment comprises a dialysis against water across a membrane with a cutoff threshold of 6,000 to 8,000 Daltons, followed by a lyophilization in order to obtain a lyophilisate.

5. The process according to claim 4, wherein the physical separation treatment comprises a centrifugation and a filtration prior to dialysis.

* * * * *